United States Patent
Fewkes et al.

(10) Patent No.: US 9,744,253 B2
(45) Date of Patent: Aug. 29, 2017

(54) ANTI-BACTERIAL LIGHT DELIVERY SYSTEM AND METHOD FOR DISINFECTING A SURFACE

(71) Applicant: CORNING INCORPORATED, Corning, NY (US)

(72) Inventors: Edward John Fewkes, Corning, NY (US); Stephan Lvovich Logunov, Corning, NY (US); Cynthia Jean Wilson, Corning, NY (US)

(73) Assignee: CORNING INCORPORATED, Corning, NY (US)

( * ) Notice: Subject to any disclaimer, the term of this patent is extended or adjusted under 35 U.S.C. 154(b) by 18 days.

(21) Appl. No.: 15/001,641

(22) Filed: Jan. 20, 2016

(65) Prior Publication Data

US 2016/0136311 A1    May 19, 2016

Related U.S. Application Data (62) Division of application No. 14/540,265, filed on Nov. 13, 2014, now Pat. No. 9,278,148.

(60) Provisional application No. 61/908,915, filed on Nov. 26, 2013.

(51) Int. Cl.
  *A61L 2/10*   (2006.01)
  *A61L 2/08*   (2006.01)

(52) U.S. Cl.
  CPC ............. *A61L 2/088* (2013.01); *A61L 2/085* (2013.01); *A61L 2/10* (2013.01)

(58) Field of Classification Search
  CPC .......................................................... A61L 2/10
  USPC ............................................................ 422/24
  See application file for complete search history.

(56) References Cited

U.S. PATENT DOCUMENTS

| | | | |
|---|---|---|---|
| 5,637,877 A | * | 6/1997 | Sinofsky .................. A61L 2/10 250/492.1 |
| 5,875,384 A | | 2/1999 | Peill et al. |
| 6,094,767 A | | 8/2000 | Iimura |
| 6,239,442 B1 | | 5/2001 | Iimura |
| 6,258,736 B1 | | 7/2001 | Massholder |
| 6,282,349 B1 | * | 8/2001 | Griffin ................. G02B 6/3813 385/81 |
| 6,524,529 B1 | | 2/2003 | Horton, III |

(Continued)

FOREIGN PATENT DOCUMENTS

| | | |
|---|---|---|
| EP | 2586466 A1 | 1/2013 |
| WO | 9607451 A2 | 3/1996 |

(Continued)

OTHER PUBLICATIONS

International Search Report, issued in connection with corresponding PCT application No. PCT/US2014/065381, Feb. 19, 2015.

*Primary Examiner* — Sean E Conley (57) ABSTRACT

A light delivery system and method are provided to promote a photochemical reaction for disinfecting a surface. The system includes a light source and a light diffusing element operatively coupled to the light source and further embedded within a surface to be disinfected. The light diffusing element outputs light to the surface to promote a photochemical reaction to disinfect the surface. A low scatter light transmission medium may further be coupled between the light source and the light diffusing element to transmit light from the light source remotely to the light diffusing element.

20 Claims, 5 Drawing Sheets

(56) References Cited

U.S. PATENT DOCUMENTS

| | | |
|---|---|---|
| 7,450,806 B2 | 11/2008 | Bookbinder et al. |
| 7,505,660 B2 | 3/2009 | Bickham et al. |
| 7,930,904 B2 | 4/2011 | Bookbinder et al. |
| 8,431,910 B1 | 4/2013 | Perry |
| 2006/0206997 A1 | 9/2006 | Chiang et al. |
| 2007/0266738 A1 | 11/2007 | Gallagher et al. |
| 2011/0152750 A1 | 6/2011 | Dacey, Jr. et al. |
| 2011/0291995 A1 | 12/2011 | Shr et al. |
| 2011/0305035 A1 | 12/2011 | Bickham et al. |
| 2012/0040600 A1* | 2/2012 | Ortner .................... A41D 13/02 454/187 |
| 2012/0191031 A1 | 7/2012 | Quisenberry |
| 2013/0035629 A1 | 2/2013 | Soltz et al. |
| 2013/0048877 A1* | 2/2013 | Thoren .................. G02B 6/102 250/492.1 |
| 2013/0115131 A1 | 5/2013 | Hegg et al. |

FOREIGN PATENT DOCUMENTS

| | | |
|---|---|---|
| WO | 2010011299 A2 | 1/2010 |
| WO | 2011063214 A1 | 5/2011 |

* cited by examiner

ANTI-BACTERIAL LIGHT DELIVERY SYSTEM AND METHOD FOR DISINFECTING A SURFACE

CROSS-REFERENCE TO RELATED APPLICATIONS

This application is a divisional of U.S. patent application Ser. No. 14/540,265 filed Nov. 13, 2014, which claims the benefit of priority under 35 U.S.C. §119 of U.S. Provisional Application Ser. No. 61/908,915 filed on Nov. 26, 2013, both of which are hereby incorporated by reference for all purposes as if fully set forth herein.

BACKGROUND

This disclosure pertains to a light delivery system to promote photochemical reaction for disinfecting a surface to provide a sterile environment.

Anti-bacterial applications or disinfectants are commonly applied to surfaces, such as surgery tables or other surfaces in clean rooms and other environments to provide sterile surfaces. Known anti-bacterial treatments typically involve applying an anti-bacterial lotion or liquid to the surface to kill bacteria to thereby decontaminate and clean the surface. It is desirable to provide a means for disinfecting a surface that does not require the time and expense of applying an anti-bacterial lotion or liquid to the surface.

SUMMARY

In accordance with one embodiment, a light delivery system to promote a photochemical reaction for disinfecting a surface is provided. The system includes a light source and a light diffusing element operatively coupled to the light source and further embedded within a surface to be disinfected. The light diffusing element outputs light to the surface to promote a photochemical reaction to disinfect the surface.

In accordance with another embodiment, a method of disinfecting a surface by promoting a photochemical reaction is provided. The method includes the steps of coupling a light diffusing element to a surface to be disinfected, supplying light having a wavelength to promote a photochemical reaction to the light diffusing element, and applying the light output from the light diffusing element to the surface to promote a photochemical reaction to disinfect the surface.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiments, and together with the description serve to explain principles and operation of the various embodiments.

DETAILED DESCRIPTION

Reference will now be made in detail to the present preferred embodiments, examples of which are illustrated in the accompanying drawings. Whenever possible, the same reference numerals will be used throughout the drawings to refer to the same or like parts.

The following detailed description represents embodiments that are intended to provide an overview or framework for understanding the nature and character of the claims. The accompanied drawings are included to provide a further understanding of the claims and constitute a part of the specification. The drawings illustrate various embodiments, and together with the descriptions serve to explain the principles and operations of these embodiments as claimed.

Referring to FIGS. 1-4, a light delivery system 10 is illustrated for promoting a photochemical reaction for disinfecting a surface 12 of an object, such as the work surface of a table 15. The light delivery system 10 employs an active light and an optional photocatalyst to promote a photochemical reaction in the volume on the surface 12 of the table 15 to disinfect the table surface. The light applied to illuminate the surface 12 may include light having a wavelength that serves to kill germs or inhibit the growth of microorganisms such as bacteria. The light may be used alone or may be used in combination with a photocatalyst such as rutile $TiO_2$. The light wavelength may be in the range of 200 nm to 2000 nm, according to one embodiment. According to a specific embodiment, an ultraviolet (UV) light having a wavelength in the range of 200 to 400 nm may be used. The light may include a combination of wavelengths and may include a red laser light that is known to help increase sterility. Further, combinations of infrared (IR) light can also be used as an additional heat source for accelerating the photochemical processes.

The light delivery system 10 includes at least one electrically powered light source 16 for generating and supplying an active light with select wavelength(s) to promote the photochemical reaction. The light source 16 may be a collimated or Lambertian light source. The light source 16 may include one or more lasers, light emitting diodes (LEDs), incandescent bulbs, ultraviolet lamps or a combination of light sources. The light source(s) 16 may generate light having a unique color or may combine various colors, such as red, green and blue light sources to generate custom colors. In one embodiment, one or more ultraviolet light sources are employed.

Figure 3:
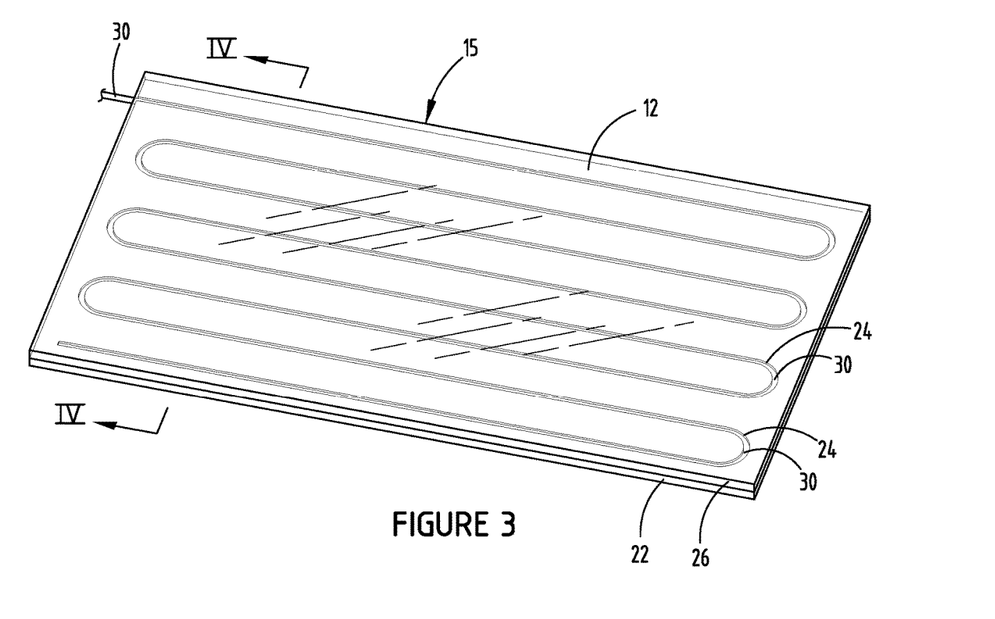
FIG. 3 is a perspective view illustrating the light diffusing element embedded in a channel in the surface of a table, according to one embodiment.
Figure 4:
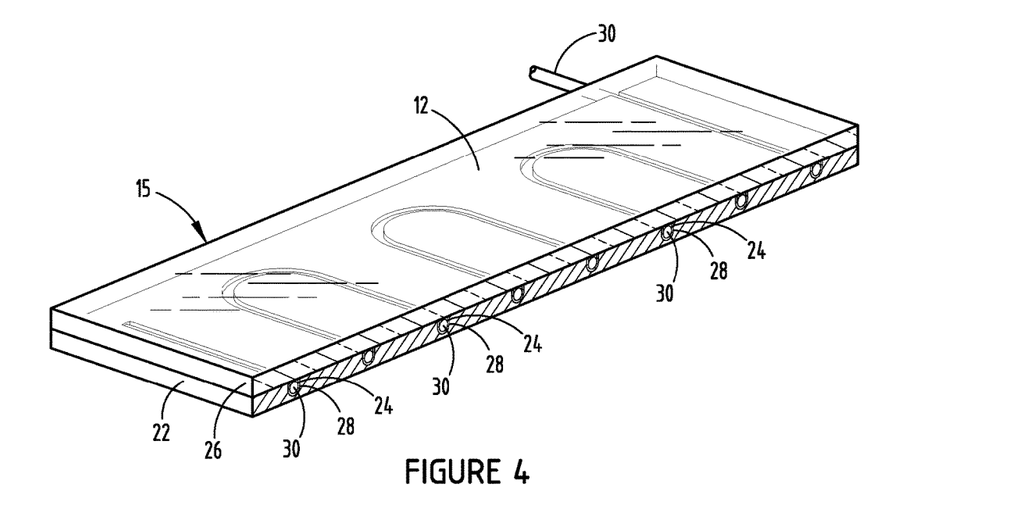
FIG. 4 is a cross-sectional view taken through line IV-IV of FIG. 3 further illustrating the table.

The light delivery system 10 also includes at least one light diffusing element 30 operatively coupled to the light source 16 to receive the light supplied by the light source 16 and disperses the light. The light diffusing element 30 is embedded within surface 12 of the table 15 to be disinfected. The light diffusing element 30 is a high scatter light transmission fiber that receives the light generated by light source 16 and scatters and outputs the light to the surface 12 to promote a photochemical reaction to disinfect the surface 12. The high scatter light transmission achieved with the light diffusing element 30 has a light attenuation of 0.5 dB/meter or greater. The light diffusing element 30 may include one or more light diffusing fibers, according to one embodiment, disposed within a channel 24 or within a plurality of channels 24 formed in the table 15 such as are shown in FIGS. 3 and 4. According to another embodiment, the light diffusing element 30 may include one or more light diffusing rods.

The surface 12 may be the top work surface of a table 15 such as a surgical or operating table, a laboratory table, a countertop table in the home or office, or any other table surface. The surface 12 may be associated with other objects such as toilet seats, handles, and other objects, according to other embodiments. In one exemplary embodiment, the surface 12 may be the work surface of a table 15 used in a clean room 14 (e.g., operating room) for hospitals. The table 15 includes a panel 22 having a top surface, a bottom surface, an edge around the periphery and channels 24 shown formed in the top surface for receiving the light diffusing element 30. A light transmissive cover 26 may be disposed on top of panel 22 to allow light generated by the light diffusing element 30 to illuminate the top surface 12. The cover 26 may be translucent such that the light is transmitted through the cover 26 and diffused. A reflective surface 28 may be provided on the inner side walls and bottom wall of channels 24 to reflect the light upwards towards the top surface 12. In one embodiment, the panel 22 may include a metal material and the cover 26 may include a glass overlay and the metal panel 22 may include light reflective proportions to eliminate the need for an additional reflective surface. The channel(s) 24 and light diffusing element 30 may be arranged in various shapes and sizes to properly illuminate select areas or the entire surface to be disinfected. While the table 15 shown is rectangular, it should be appreciated that other shapes and sizes may be used.

The light delivery system 10 may further include a low scatter light transmission medium 18 coupled between the light source 16 and the light diffusing element 30. According to one embodiment, the low scatter light transmission medium 18 may include an optical fiber designed to transmit light with low signal loss. The low scatter light transmission achieved with the transmission medium 18 has a light attenuation of less than 0.5 dB/meter. The low scatter light transmission medium 18 is shown in one embodiment coupled to the light diffusing element 30 by way of an optical coupler 20. It should be appreciated that the low scatter light transmission medium 18 may otherwise be operatively coupled to the light diffusing element 30 using various optical connections including splices, butt couplings and other light transmission couplings.

Figures 1, 2:
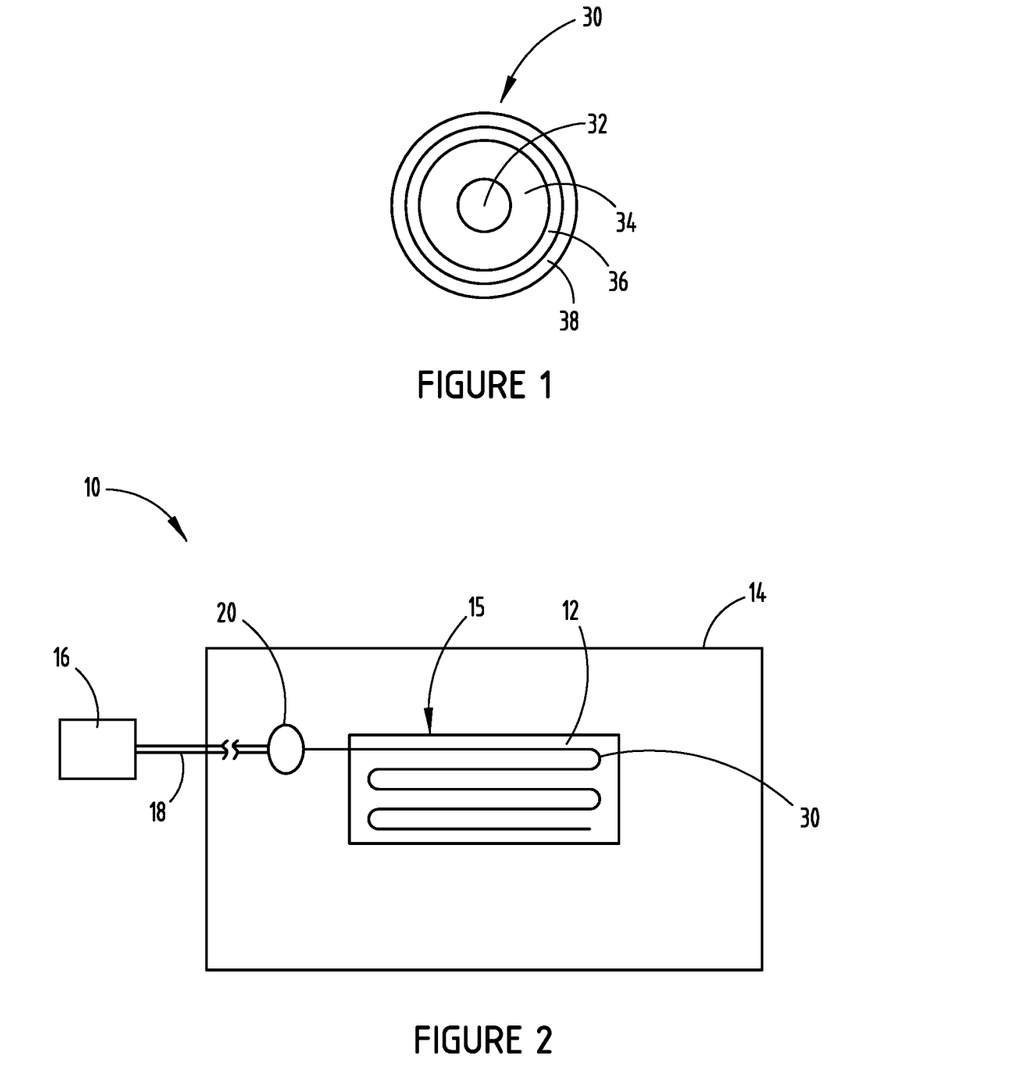
FIG. 1 is a diagrammatic cross-sectional view of one embodiment of a light diffusing fiber useful as a light diffusing element in a light delivery system.
FIG. 2 is a top schematic diagram illustrating a light delivery system for promoting photochemical reaction for disinfecting a surface with the use of the light diffusing element, according to one embodiment.

In the embodiment shown in FIG. 2, the surface 12, such as the work surface of an operating table 15, is shown located within a clean room 14, whereas the electrically powered light source 16 is located outside of the clean room 14. The low scatter light transmission medium 18 advantageously allows light generated by the light source 16 to be transmitted a substantial distance with low light signal loss into the clean room 14 to the light diffusing element 30 where the light is diffused and transmitted to the surface 12 of table 15 for disinfecting the surface 12. As such, the light diffusing element 30 may be employed as a flexible remote light illuminator that allows continuous sterilization in wet, explosive, or other sterile environments, while positioning the light source 16 outside of the clean room 14. As such, the light source 16 does not need to be sterilized and may be electrically powered from outside the clean room 14.

The low scatter light transmission medium 18 may include a transmission fiber that may be a single fiber, a bundled (or ribbonized) collection of fibers, a plastic optical fiber (POF), or other light transmission medium. The low scatter light transmission medium 18 may employ a fused silica rod, according to another embodiment, that can also be used as efficient delivery of light from the light source 16 to the light diffusing element 30. The low scatter transmission medium 18 may be connected to the light diffusing element 30 by the optical coupler 20 or by butt coupling to the light diffusing element 30.

The light diffusing element 30 may be configured as a single light diffusing fiber or may be bundled (or ribbonized) collections of light diffusing fibers. The light diffusing fiber 30 may be flexible, thus allowing ease in installation within the channel 24. In one embodiment, the light diffusing fiber 30 has a diameter of 1,000 microns or less, and more particularly of about 250 microns. In other embodiments, the light diffusing fiber 30 may be more rigid such as in the form of a light diffusing rod having a diameter greater than 1,000 microns.

One embodiment of a light diffusing fiber 30 is illustrated having a typical cross-sectional structure shown in FIG. 1. The light diffusing fiber 30 may include the formation of random air lines or voids in one of the core and cladding of a silica fiber. Examples of techniques for designing and forming such light diffusing fibers may be found, for example, in U.S. Pat. Nos. 7,450,806; 7,930,904; and 7,505,660, and U.S. Patent Application Publication No. 2011/0305035, which are hereby incorporated by reference. The light diffusing fiber 30 has a glass core 32 which may include an F-doped core. An $SiO_2$ cladding layer 34 having air lines for scattering light is shown surrounding the core 32. The cladding layer 34 may be formed to include air lines or voids to scatter the light and direct the light through the side walls. It should be appreciated that the random air lines 34 may be disposed in the core 32 or in the cladding 36 or in both, according to various embodiments. It should be appreciated that high scattering losses are generally preferred in the light diffusing fiber 30. A low index polymer primary protective layer 36 generally surrounds the cladding layer 34. Additionally, an outer secondary layer 38 may be disposed on the primary protective layer 36. Primary protective layer 36 may be soft and liquidy, while secondary layer 38 may be harder.

The secondary layer 38 may include a photoreactive agent according to one embodiment. The photoreactive agent may be provided as the secondary coating having a hardness greater than the first cladding coating. The photoreactive agent may include materials such as $TiO_2$, $W_2O_3$, and other catalytic elements that photo-oxidizes when the light activates the material.

Scattering loss of the light diffusing fiber 30 may be controlled throughout steps of fiber manufacture and processing. During the air line formation process, the formation of a greater number of bubbles will generally create a larger amount of light scatter, and during the draw process the scattering can be controlled by using high or low tension to create higher or lower loss, respectively. To maximize loss of light, a polymeric cladding may be desirably removed as well, over at least a portion of the light diffusing fiber 30 length if not all. Uniform angular loss in both the direction of light propagation, as well as in the reverse direction can be made to occur by coating the light diffusing fiber 30 with inks that contain scattering pigments or molecules, such as $TiO_2$. An ultraviolet light source may be used as well, with a fluorescent dye or phosphor materials applied to the fiber cladding (effectively down converting the ultraviolet wavelength of light with approximately 100 percent efficiency to a desired wavelength). Use of such fluorescence down-conversion creates very uniform angular light distribution. The high scattering light diffusing fiber 30 may have a modified cladding to promote scattering and uniformity. Intentionally introduced surface defects on the light diffusing fiber 30 or core or cladding may also be added to increase light output, if desired.

The light diffusing fiber 30 may have a region or area with a large number (greater than 50) of gas filled voids or other nano-sized structures, e.g., more than 50, more than 100, or more than 200 voids in the cross section of the fiber. The gas filled voids may contain, for example, $SO_2$, Kr, Ar, $CO_2$, $N_2$, $O_2$, or mixture thereof. The cross-sectional size (e.g., diameter) of the nano-size structures (e.g., voids) may vary from 10 nanometers to 1 micrometer (for example, 15 nanometers to 500 nanometers), and the length may vary depending on the area of the surface to be disinfected.

While the light diffusing fiber 30 is shown and described herein having air lines, it should be appreciated that other light scattering features may be employed. For example, high index materials such as $GeO_2$, $TiO_2$, $ZrO_2$, ZnO, and others may be employed to provide high scatter light transmission. It should further be appreciated the light diffusing element 30 may be a light diffusing rod that is less flexible, has a larger diameter and may have no coating.

Figure 5:
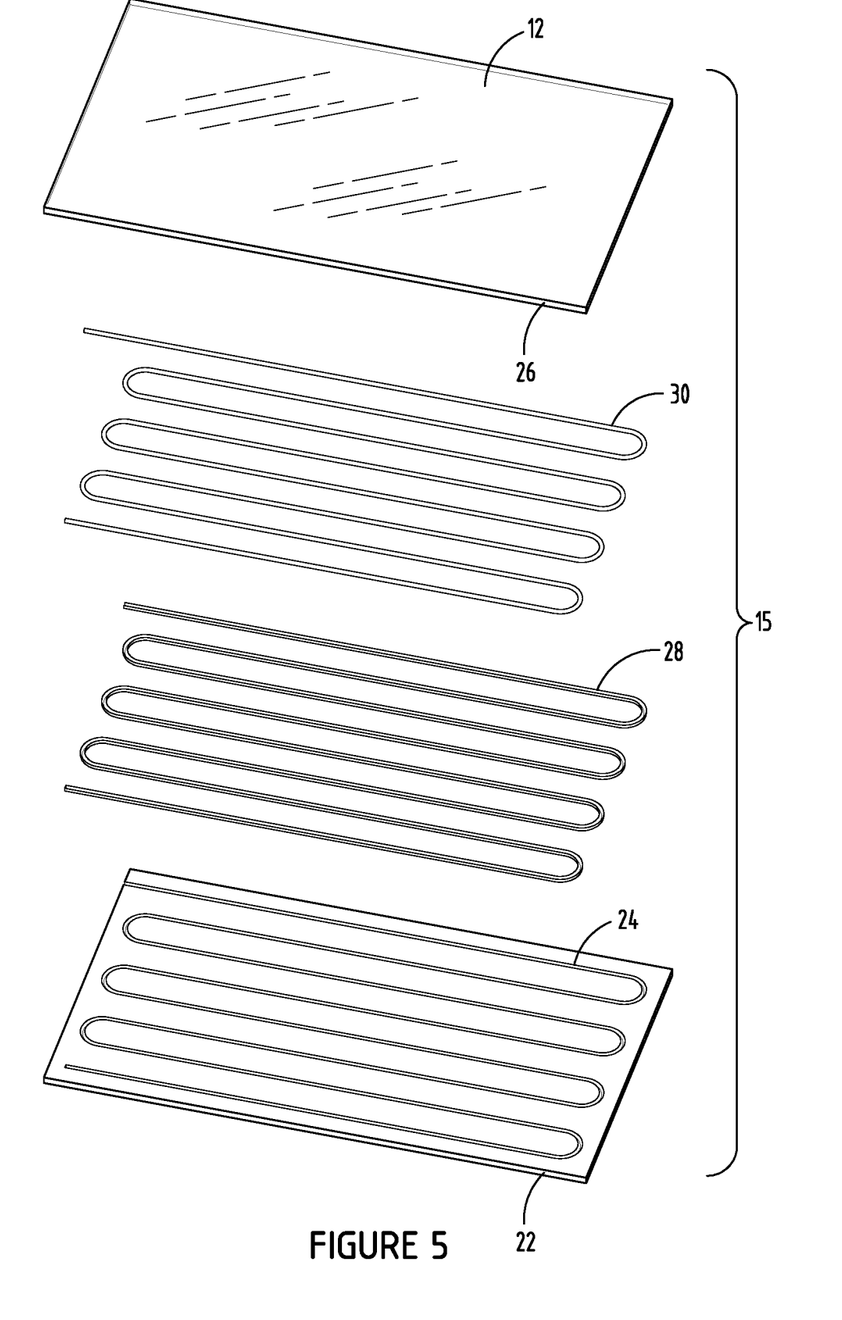
FIG. 5 is an exploded view of the table and the embedded light diffusing element of FIG. 3.
Figure 6:
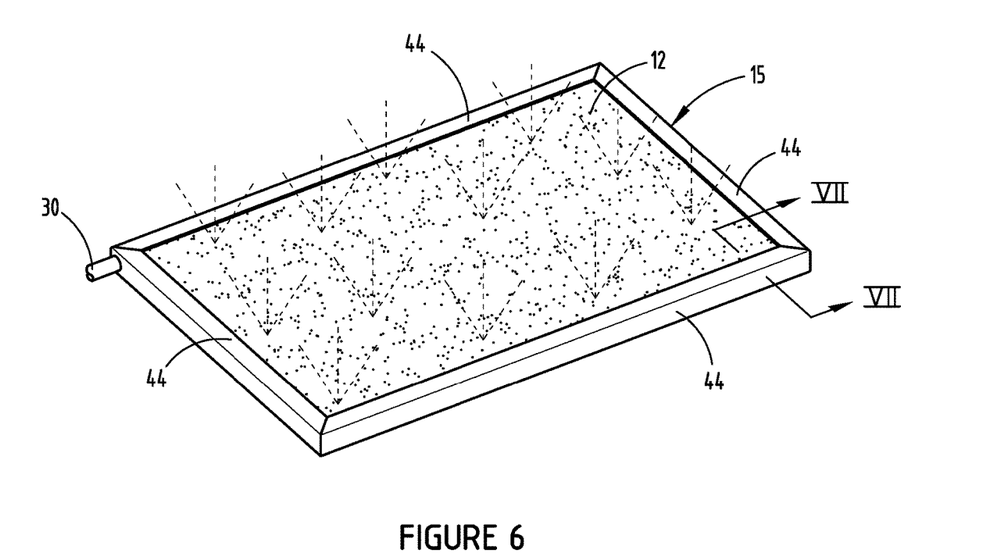
FIG. 6 is a perspective view of a light delivery system employing the light diffusing element embedded in a table around a perimeter of the table surface, according to a second embodiment.
Figure 7:
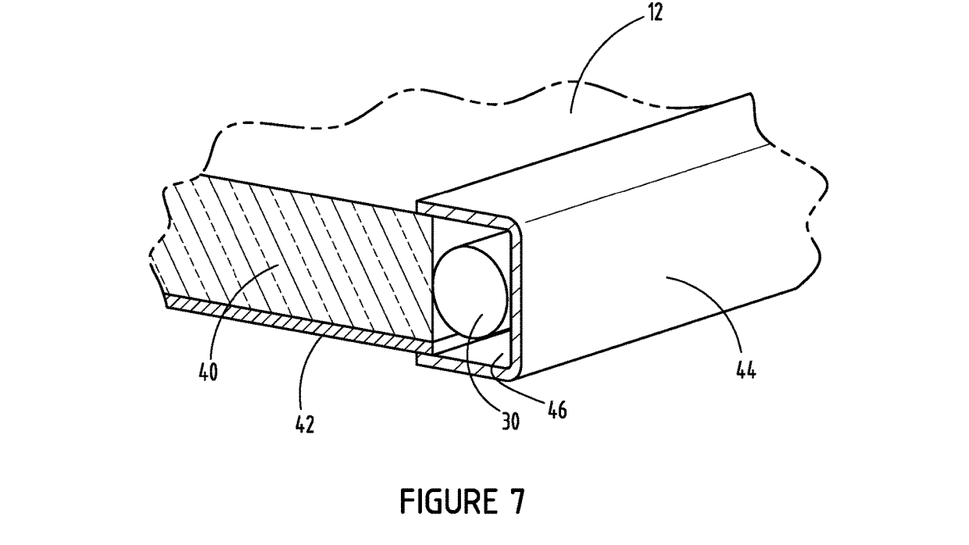
FIG. 7 is a cross-sectional view taken through line VI-VI of FIG. 5 further illustrating the table.
Figure 8:
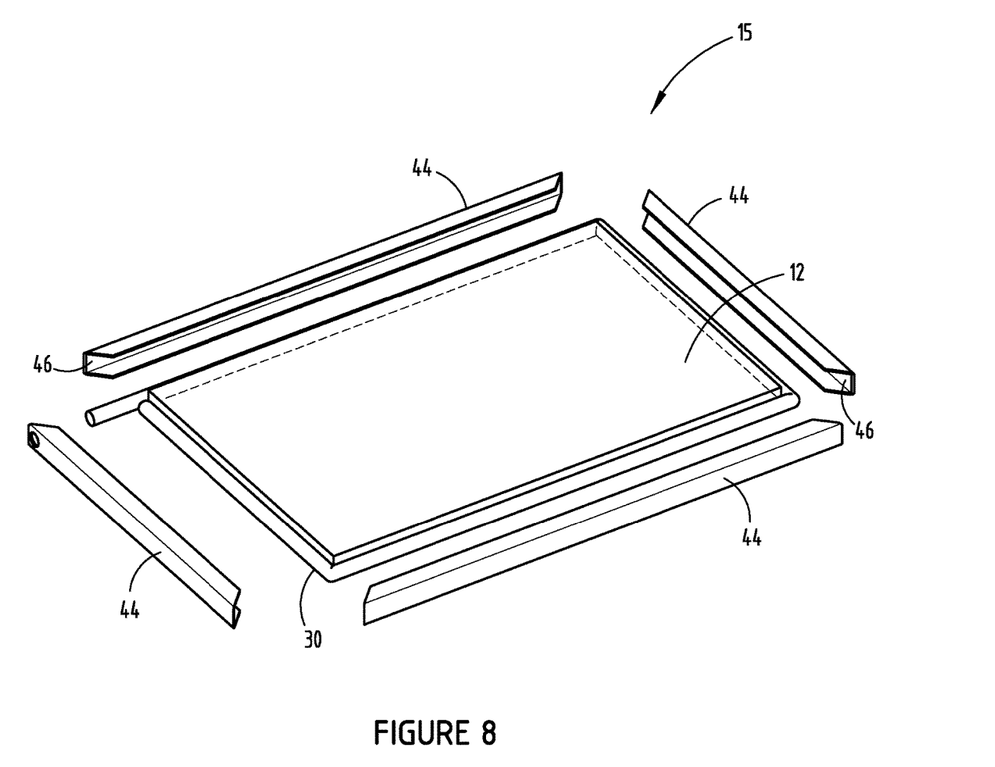
FIG. 8 is an exploded view of the table and work surface further illustrating the arrangement of the light diffusing element embedded around the perimeter of the table and work surface shown in FIG. 5.

Referring to FIGS. 5-7, a light delivery system 10, according to another embodiment is illustrated employing a light diffusing element 30 extending within the surface 12 and around the periphery of a table 15 having a surface 12 to be disinfected. The light diffusing element 30 may be a light diffusing fiber or light diffusing rod and is shown extending along all four side edges of a light transmissive medium 40, such as a glass panel. As such, the light diffusing element 30 edge lights the glass panel so that light passing through the light diffusing element 30 is effectively illuminated into the glass medium. The glass medium 40 may be made of a translucent material so that the light further diffuses and illuminates the top surface. Additionally, the bottom surface of the glass medium 40 has a reflective surface 42 for reflecting light upward towards surface 12 to be disinfected. Additionally, edge coverings 44 are disposed along the peripheral edges of the table outside of the light diffusing element 30 and may include an internal reflective surface 46 to reflect light back into the glass medium 40. As such, light passing through the light diffusing element 30 is reflected upwards by the bottom surface and inwards by the edge coverings 44 into the glass medium 40 from where it propagates up to surface 12 to be disinfected.

A method of disinfecting a surface by promoting a photochemical reaction with the use of the light delivery system 10 will now be described. The method includes the step of coupling a light diffusing element 30 to a surface 12 to be disinfected. The surface 12 may be a table 15, such as an operating table used within a clean room. The method also includes the step of supplying light having a wavelength to promote a photochemical reaction to the light diffusing element 30. The method further includes the step of applying the light output from the light diffusing element 30 to the surface 12 to promote a photochemical reaction to disinfect the surface 12.

The method may further include the step of supplying the light from a light source 16 to a low scatter light transmission medium 18, and further coupling the low scatter light transmission medium 18 to the light diffusing element 30. The light diffusing element 30 may be disposed within a channel 24 formed in the surface 12. The surface 12 may be disposed within a clean room 14 and the light source 16 may be disposed outside of the clean room 14. The light diffusing element 30 may be a light diffusing fiber having a glass core, a cladding, and a plurality of air lines disposed in one of the core and the cladding. The cladding may include a coating comprising a photoreactive agent.

Accordingly, the light delivery system 10 and method advantageously delivers light from a light source 16 to a light diffusing element 30 embedded within a surface 12 such as a table 15 to disinfect the surface 12 with light generated by the light source 16. As such, the surface 12 may be disinfected with light that is generated remotely and transmitted to the surface by way of the light diffusing element 30 in a manner that is safe, easy to use and clean.

Various modifications and alterations may be made to the examples within the scope of the claims, and aspects of the different examples may be combined in different ways to achieve further examples. Accordingly, the true scope of the claims is to be understood from the entirety of the present disclosure in view of, but not limited to, the embodiments described herein.

It will be apparent to those skilled in the art that various modifications and variations can be made without departing from the spirit or scope of the claims.

What is claimed is:

1. A method of disinfecting a target surface by promoting a photochemical reaction at the target surface, the method comprising:
   optically coupling a light diffusing fiber to the target surface to be disinfected by disposing the light diffusing fiber into one or more channels disposed in a surface of a panel, wherein:
      a light transmissive cover is positioned over the one or more channels; and
      a reflective surface is positioned within the one or more channels between the one or more channels and the light diffusing fiber;
   supplying light to the light diffusing fiber having a wavelength configured to promote a photochemical reaction at the target surface; and
   applying the light output from the light diffusing fiber to the target surface to promote a photochemical reaction at the target surface to disinfect the target surface, wherein the light diffusing fiber comprises a glass core, a cladding, and a plurality of light scattering features.

2. The method of claim 1 further comprising:
   supplying the light from a light source to a low scatter light transmission medium; and
   coupling the low scatter light transmission medium to the light diffusing fiber.

3. The method of claim 1, wherein the target surface is disposed within a clean room and the light source is disposed outside of the clean room.

4. The method of claim 1, wherein the cladding comprises a coating comprising a photoreactive agent.

5. The method of claim 1, wherein the plurality of light scattering features comprise a plurality of air lines.

6. The method of claim 1, wherein the light diffusing fiber is positioned about a periphery of the panel, the light transmissive cover, or both.

7. The method of claim 1, wherein the target surface is on a surgical table.

8. The method of claim 1, wherein the light source generates light having at least one wavelength in the range of between 200 nm and 2000 nm.

9. The method of claim 1, wherein the light source generates ultraviolet light.

10. The method of claim 1, wherein the light diffusing fiber further comprises a primary layer surrounding the cladding and a secondary layer disposed on the primary layer.

11. The method of claim 10, wherein the primary layer comprises a polymer.

12. The method of claim 10, wherein the secondary layer is harder than the primary layer.

13. The method of claim 1, wherein the target surface comprises a surface of the light transmissive cover.

14. A method of disinfecting a target surface by promoting a photochemical reaction at the target surface, the method comprising:
optically coupling a light diffusing fiber to the target surface to be disinfected by disposing the light diffusing fiber about one or more peripheral edges of a light transmissive medium, wherein:
one or more edge coverings are disposed along the one or more peripheral edges of the light transmissive medium; and
the light diffusing fiber is positioned between the one or more edge coverings and the one or more peripheral edges of the light transmissive medium;
supplying light to the light diffusing fiber having a wavelength configured to promote a photochemical reaction at the target surface; and
applying the light output from the light diffusing fiber to the target surface to promote a photochemical reaction at the target surface to disinfect the target surface, wherein the light diffusing fiber comprises a glass core, a cladding, and a plurality of light scattering features.

15. The method of claim 14, wherein the light transmissive medium comprises a reflective surface positioned opposite the target surface.

16. The method of claim 14, wherein the one or more edge coverings comprise an internal reflective surface facing the light diffusing fiber.

17. The method of claim 14 further comprising:
supplying the light from a light source to a low scatter light transmission medium; and
coupling the low scatter light transmission medium to the light diffusing fiber.

18. The method of claim 14, wherein the cladding comprises a coating comprising a photoreactive agent.

19. The method of claim 14, wherein the plurality of light scattering features comprise a plurality of air lines.

20. The method of claim 14, wherein the target surface comprises a surface of the light transmissive medium.

* * * * *